US008617652B2

(12) United States Patent
Lee (10) Patent No.: US 8,617,652 B2
(45) Date of Patent: Dec. 31, 2013

(54) DEPOSITING MATERIAL ON FIBROUS TEXTILES USING ATOMIC LAYER DEPOSITION FOR INCREASING RIGIDITY AND STRENGTH

(75) Inventor: Sang In Lee, Sunnyvale, CA (US)

(73) Assignee: Veeco ALD Inc., Fremont, CA (US)

( * ) Notice: Subject to any disclaimer, the term of this patent is extended or adjusted under 35 U.S.C. 154(b) by 0 days.

(21) Appl. No.: 13/536,646

(22) Filed: Jun. 28, 2012

(65) Prior Publication Data

US 2013/0023172 A1    Jan. 24, 2013

Related U.S. Application Data

(60) Provisional application No. 61/511,025, filed on Jul. 23, 2011.

(51) Int. Cl.
*C23C 16/30* (2006.01)
(52) U.S. Cl.
USPC ........ 427/255.31; 427/255.391; 427/255.394; 427/255.29; 427/249.1; 427/376.1; 427/376.2; 427/569
(58) Field of Classification Search
USPC ........... 427/255.31, 255.391, 255.394, 255.7, 427/376.1, 376.2, 569, 255.29, 249.1
See application file for complete search history.

(56) References Cited

U.S. PATENT DOCUMENTS

| 5,572,725 | A | 11/1996 | Morris et al. |
| 6,632,516 | B2 | 10/2003 | Aanestad |
| 7,060,132 | B2 | 6/2006 | Lindfors et al. |
| 7,560,793 | B2 | 7/2009 | Derderian et al. |
| 2004/0076751 | A1 | 4/2004 | Sherman |
| 2006/0081525 | A1* | 4/2006 | Lobovsky et al. ........ 210/321.88 |
| 2008/0102259 | A1* | 5/2008 | Nikolov et al. ............... 428/213 |
| 2008/0119098 | A1 | 5/2008 | Palley et al. |
| 2009/0000541 | A1 | 1/2009 | Conley |
| 2009/0081827 | A1 | 3/2009 | Yang et al. |
| 2009/0137043 | A1* | 5/2009 | Parsons et al. ................ 435/398 |
| 2009/0165715 | A1 | 7/2009 | Oh |
| 2011/0014795 | A1 | 1/2011 | Lee et al. |
| 2011/0076421 | A1 | 3/2011 | Lee |
| 2011/0159764 | A1 | 6/2011 | Price et al. |

FOREIGN PATENT DOCUMENTS

KR    10-2006-0117607 A    11/2006

OTHER PUBLICATIONS

Jur, Jesse S., et al., "Atomic Layer Deposition of Al2O3 and ZnO at Atmospheric Pressure in a Flow Tube Reactor". ACS Appl. Mater. Interfaces 2011, 3, 299-308.*

(Continued)

*Primary Examiner* — Bret Chen
(74) *Attorney, Agent, or Firm* — Fenwick & West LLP (57) ABSTRACT

Embodiments relate to depositing on one or more layers of materials on a fiber or fiber containing material using atomic layer deposition (ALD) to provide or enhance functionalities of the fibers or fiber containing material. A layer of material is deposited coated on the fibers or fiber containing textile by causing the relative movement between a fiber or the fiber containing textile and a source injector. The surface of the material is oxidized, nitrified or carbonized to increase the volume of the deposited material. By increasing the volume of the material, the material is subject to compressive stress. The compressive stress renders the fibers or the fiber containing material more rigid, stronger and more resistant against bending force, impact or tensile force.

11 Claims, 5 Drawing Sheets

(56) References Cited

OTHER PUBLICATIONS

Hojo, Daisuke, et al., "3-Dimensional Al2O3 Fiber Networks using Low Temperature Atomic Layer Deposition on a Cotton Template". Mater. Res. Soc. Symp. Proc. vol. 1054, 1054-FF03-08, 2008, pp. 1-6.*

PCT International Search Report and Written Opinion, PCT Application No. PCT/US12/44839, Sep. 24, 2012, 11 pages.

Kariniemi, M, et al., "Plasma-Enhanced Atomic Layer Deposition of Silver Thin Films," Chemistry of Materials, 2011, p. 2901-2907, vol 23.

Niskanen, A. et al., "Radical-Enhanced Atomic Layer Deposition of Silver Thin Films Using Phosphine-Adducted Silver Carboxylates," Chemical Vapor Deposition, 2007, p. 408-413, vol. 13.

* cited by examiner

DEPOSITING MATERIAL ON FIBROUS TEXTILES USING ATOMIC LAYER DEPOSITION FOR INCREASING RIGIDITY AND STRENGTH

CROSS-REFERENCE TO RELATED APPLICATION

This application claims priority under 35 U.S.C. §119(e) to co-pending U.S. Provisional Patent Application No. 61/511,025, filed on Jul. 23, 2011, which is incorporated by reference herein in its entirety.

BACKGROUND

1. Field of Art

The disclosure relates to depositing materials on fibers or textiles using atomic layer deposition to increase rigidity or afford other useful characteristics to the fibers or the textiles.

2. Description of the Related Art

Figure 1:
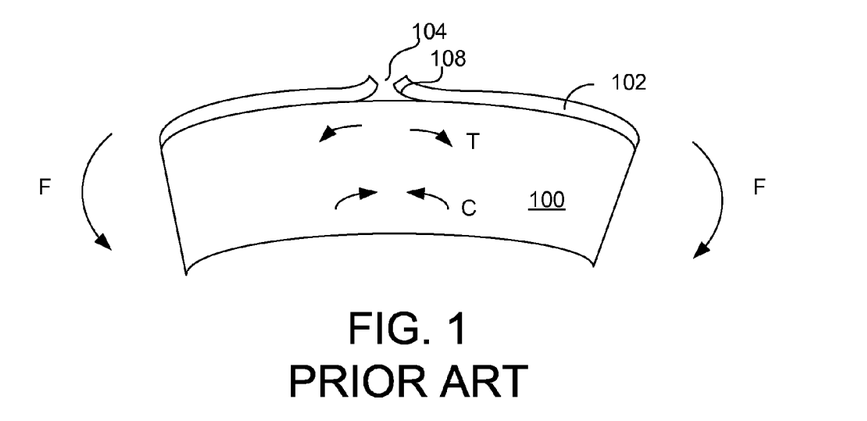
FIG. 1 is a cross sectional view showing the internal stress in a conventional fiber and the failure of coated materials on the fiber.

A fiber generally lacks sufficient strength or rigidity for various applications. Hence, multiple fibers are often interlocked into yarn for higher strength and rigidity. The yarn is then used for producing textiles, crochet, knits, and ropes. Alternatively, fibers (e.g., carbon fibers) can be combined with other materials (e.g., polymer) to produce composites that are strong yet economically viable. Example of such composites include, among others, carbon-fiber-reinforced polymer (CFRP). CFRP may include Kevlar, aluminum or glass fibers in addition to carbon fibers for increased strength and improved properties To increase strength or rigidity, fibers may be coated with materials. However, such fibers tend to form cracks or other defects on their surfaces when the fibers are bent beyond a certain curvature or stretched beyond an extent. FIG. 1 is a cross-sectional diagram of a fiber 100 coated with a material 102 subject to bending force F. As the fiber 100 is bent (as illustrated in FIG. 1), the upper part of the fiber 100 and the coated material 102 is subject to tensile stress (denoted by "T" in FIG. 1) whereas the lower part of fiber 100 is subject to compression stress (denoted by "C" in FIG. 1). When the tensile stress exceeds a certain limit (e.g., when the fiber 100 is bent beyond an angle), the coated materials may crack due to cohesive failure (shown by reference numeral 104) and adhesive failure (shown by reference numeral 108). Similar cracks may occur when the fiber 100 and the coated material 102 are pulled or otherwise subject to tensile stress. Cracks formed on the coated materials result in reduced strength or rigidity of the fibers in addition to deterioration of functions provided by these coated materials.

When thin fibers are used, conventional methods of coating the materials on the fibers may be inadequate. That is, the materials may not become coated in a conformal manner on the fibers and the thickness of the coated materials may not be sufficiently thin to achieve the desired functionalities and properties.

SUMMARY

Embodiments relate to depositing material on a fiber or a fiber containing material to increase strength or rigidity of the fiber or the fiber containing material. Source precursor is injected onto the fiber or the fiber containing material followed by injection of reactant precursor on the fiber or the fiber containing material to deposit a layer of material on the surface of the fiber or the fiber containing material using atomic layer deposition (ALD). Compressive stress is induced in at least part of the layer by converting at least an outer portion of the layer to another material. The converted material has larger volume compared to the unconverted material, and therefore, introduces compressive stress in the layer.

In one embodiment, the conversion includes oxidizing, nitrifying or carbonizing the unconverted material.

In one embodiment, the deposited layer includes polycrystalline material. The compressive stress is induced by oxidizing, nitrifying or carbonizing at least part of grain boundaries and the outer surface of the polycrystalline material.

In one embodiment, the polycrystalline material layer includes at least one of semiconductor, metal compound or metal. The polycrystalline material layer may include TiN.

In one embodiment, an amorphous material layer is deposited on the surface of oxidized, nitrified or carbonized polycrystalline material layer. The amorphous material layer may include at least one of $Al_2O_3$ or $SiO_2$.

In one embodiment, the fiber comprises a carbon fiber.

In one embodiment, the reactant precursor comprises radicals generated by exposing gas to plasma.

In one embodiment, the deposited layer includes an amorphous material. The amorphous material may be $Al_2O_3$ or SiN.

Embodiments also relate to a textile comprising a plurality of fibers where each of the fibers is deposited with a layer of material on its surface using atomic layer deposition (ALD) to increase strength or rigidity. A treated layer is formed on the surface of the material by oxidizing, nitrifying or carbonizing parts of the material layer to induce compressive stress in the deposited material layer. The treated layer at least partially diffuses into the grain boundaries of the material layer. The compressive stress in the material layer increases strength or rigidity of each fiber.

In one embodiment, the deposited layer includes polycrystalline material. The compressive stress is induced by oxidizing, nitrifying or carbonizing at least part of grain boundaries and the outer surface of the polycrystalline material.

DETAILED DESCRIPTION OF EMBODIMENTS

Embodiments are described herein with reference to the accompanying drawings. Principles disclosed herein may, however, be embodied in many different forms and should not be construed as being limited to the embodiments set forth herein. In the description, details of well-known features and techniques may be omitted to avoid unnecessarily obscuring the features of the embodiments.

In the drawings, like reference numerals in the drawings denote like elements. The shape, size and regions, and the like, of the drawing may be exaggerated for clarity.

Embodiments relate to depositing one or more layers of materials on a fiber or fiber containing material using atomic layer deposition (ALD) to increase rigidity or strength to provide resistance to bending, impact or tensile force. A layer of material is deposited on the fibers or the fiber containing material and then at least part of the deposited material is oxidized, nitrified or carbonized to induce compressive stress in the material layer. The deposited material may be polycrystalline material or amorphous material. The compressive stress renders the fibers or the textile more rigid, stronger and more resistant against bending force, impact or tensile force. Further, the fibers or the textile can be coated with additional materials to prevent oxidization or prevent detection against night vision cameras.

The fiber containing material described herein refers to any material containing fibers. The fiber containing material include, for example, yarn, textile and composite material. The fibers in the fiber containing materials may or may not be interlocked with each other.

The one or more layers of materials described herein may be deposited on the fibers before or after being incorporated into the fiber containing material.

Example Fibers or Textile Coated with Materials

A fiber and fiber containing material may lack desired properties such as rigidity or strength that may lead to reduced resistance against bending force, impact or tensile force. In order to increase the rigidity or strength, the fiber or the fiber containing material may be deposited with materials that enhance the rigidity or strength. However, the deposited material is often subject to tensile stress after deposition of the material. Hence, the deposited material is vulnerable to cracks or other defects when the fiber or the fiber containing material is bent or subject to tensile stress for other reasons.

Especially, when the material deposited on the fiber or fiber containing material is polycrystalline material, the grain boundaries of the material have a higher free energy and are often in an unstable state. Further, the bonding force between the grains is generally weak. Therefore, a layer formed of polycrystalline material has an inferior barrier characteristic as well as being prone to cracks or other failures that propagate from the grain boundaries.

In one or more embodiments, the rigidity or strength of the fiber of the fiber containing material is increased by expanding the volume of the grains after the polycrystalline material is deposited on the fiber or the fiber containing material. The volume of the grains can be increased by oxidizing, nitrifying or carbonizing the surface and at least part of the grain boundaries of the polycrystalline material.

Alternatively, amorphous material may be deposited on the fiber or fiber coating material instead of depositing the fiber or fiber containing material with polycrystalline material. The outer region of the amorphous material may be oxidized, nitrified or carbonized to expand the volume and introduce compressive stress in the outer region of the material.

Figure 2A:
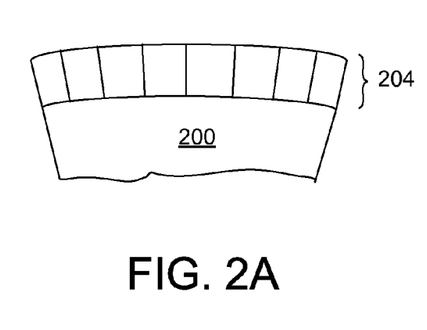
FIG. 2A is a cross sectional view of a fiber deposited with a polycrystalline material layer, according to one embodiment.

FIG. 2A is a cross sectional view of a fiber 200 deposited with a polycrystalline material layer 204, according to one embodiment. Although FIG. 2A illustrates a single fiber 200 deposited with the polycrystalline material layer 204, an entire yarn, textile or any other fiber containing material may be deposited with the polycrystalline material layer 204 using atomic layer deposition (ALD). In one embodiment, the polycrystalline material is TiN and has a thickness of 10 Å to 500 Å using a deposition device, described below in detail with reference to FIGS. 4 through 6. In other embodiments, the polycrystalline material may be one or more of semiconductor material (e.g., Si, Ge), metal (e.g., Al, Ti, Ta), metal compounds with a high melting temperature (e.g., TiAlN, TiCN, WC).

The use of ALD for depositing the polycrystalline material layer 204 is advantageous, among other reasons, because the layer 204 is deposited on the fiber 200 in a conformal manner with a thin thickness at a lower deposition temperature than other deposition methods.

The fiber 200 may be a carbon fiber or any other fibers. In an embodiment where the fiber contains carbon, the initial deposited layer may react with carbon atoms to create stronger bonding with the fiber. For example, when a carbon fiber is deposited with TiN, an initial layer of TiN film reacts with carbon atoms in the carbon fiber and forms a TiCN layer. TiCN layer advantageously increases the bonding force between the carbon fiber and TiN layer 204 further deposited on the TiCN layer.

Figure 2B:
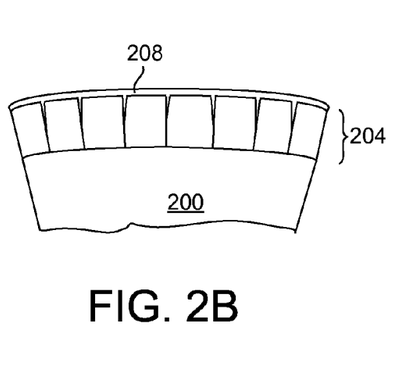
FIG. 2B is a cross sectional view of the fiber of FIG. 2A having at least part of the grain boundaries and the surface of the polycrystalline material oxidized, nitrified or carbonized, according to one embodiment.

After a polycrystalline layer of TiN 204 is formed on the TiCN layer, the fiber 200 is exposed to oxygen, $H_2O$, ozone, O* radicals or a combination thereof to oxidize the surface and grain boundaries of the TiN layer 204 into TiON. The grain boundaries of the TiN layer 204 are oxidized by diffusing these oxidizing agents into the grain boundaries. Because the extent of diffusion of oxidizing agents decreases with the depth of the TiN layer, the oxidized portion of the TiN layer 204 tends to be wider at the surface but becomes thinner as the depth towards the fiber 200 increases. As a result of the oxidization, the cross sectional shape of TiON layer 208 takes a revere triangular shape that extends at least partially into the grain boundaries of TiN layer 204.

Because TiON takes up more volume compared to TiN, the overall volume of the deposited material increases as the surface and the grain boundaries of the TiN layer 204 are oxidized into a TiON layer 208. However, since the TiN layer 204 and the TiON layer 208 are bonded to the fiber 200, the spatial expansion of these layers is restricted. As a result, these layers are instead subject to compressive stress.

Moreover, the bonding of TiON with the grains of TiN is stronger than the bonding between the grains of TiN. Therefore, cracks are less likely to occur between the boundaries of TiON and the TiN grains. As a result, the oxidization of the TiN into TiON between the boundaries further increases the strength of the fiber. In one or more embodiment, the thickness of the TiON layer is 5 to 50 Å.

TiON is also more resistant to diffusion compared to TiN. Therefore, TiON layer 208 may also function as a diffusion barrier to prevent other materials from penetrating into the fiber 200.

Alternatively, TiN layer 204 may be carbonized using, for example, C* radicals. As a result, a TiCN layer is formed on the surface of the TiN layer and also penetrates into the grain boundaries of TiN. The TiCN layer also has a larger volume compared to a TiN layer, and therefore, the formation of TiCN layer on the surface of TiN layer and penetration of TiCN into the grain boundaries cause compressive stress in TiN and TiCN layer. Further, TiCN is more resistant to diffusion compared to TiN, and therefore, TiCN also functions as a diffusion barrier for the barrier.

A layer formed by oxidizing, nitrifying or carbonizing the polycrystalline layer advantageously increases the rigidity or strength of the fiber and also functions as a diffusion barrier for the fiber.

Figure 2C:
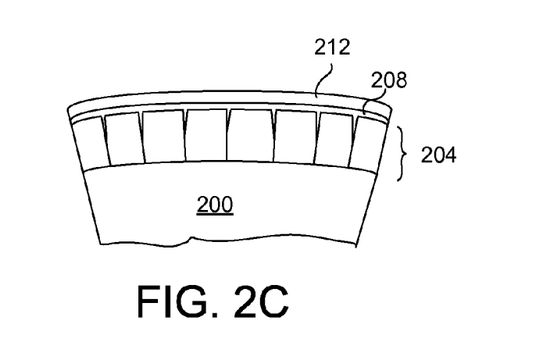
FIG. 2C is a cross sectional view of the fiber of FIG. 2B deposited with an amorphous layer, according to one embodiment.

In one embodiment, an amorphous layer is deposited on the oxidized, nitrified or carbonized polycrystalline layer. For example, a layer of $Al_2O_3$ or $SiO_2$ of 10 to 100 Å thickness is deposited on the oxidized, nitrified or carbonized polycrystalline layer. The amorphous layer reduces problems associated with coating of the polycrystalline layer because the amorphous layer may have tensile stress and the combination of different stressed films results in increased stiffness.

In one embodiment, multiple sets of layers of TiN and TiON can be deposited on the fiber or the fiber containing material. The process of depositing TiN and forming TiON may be repeated for a predetermined number of times to deposit multiple sets of TiN/TiON layer on the fiber or the fiber containing material to further increase the rigidity or strength of the fiber or the fiber containing material.

In another embodiment, multiple sets of layers, each set including a TiN layer, a TiON layer and an amorphous layer, are deposited on the fiber by repeating the process for a predetermined number of times.

Figure 3A:
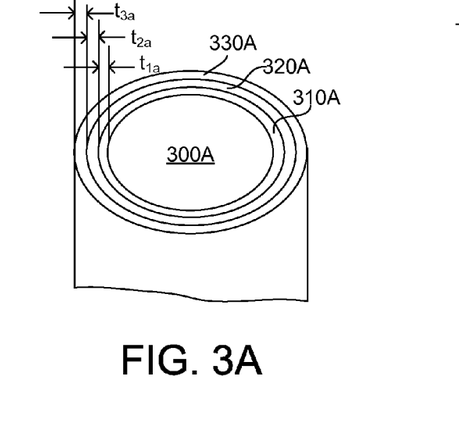
FIG. 3A is a cross sectional view of a fiber deposited with materials, according to one embodiment.

FIG. 3A is a cross sectional view of a fiber 300A deposited with materials, according to one embodiment. The fiber 300A may be a carbon fiber, which is then deposited with a first material (e.g., TiN, $Al_2O_3$, SiN) 310A of thickness $t_{1a}$, a layer 320A of thickness $t_{2a}$ formed by oxidizing, nitrifying or carbonizing the first material (e.g., TiON, TiCN, AlON, $SiO_2$), and an amorphous layer 330A of thickness $t_{3a}$. In one embodiment, the thickness of $t_{1a}$ is 10 to 500 Å, the thickness of $t_{2a}$ is 5 to 50 Å and the thickness of $t_{3a}$ is 10 to 500 Å.

The process of depositing layers 310A, 320A, 330A may be repeated for a predetermined number of cycles to deposit sets of layers on the fiber 300A.

Figure 3B:
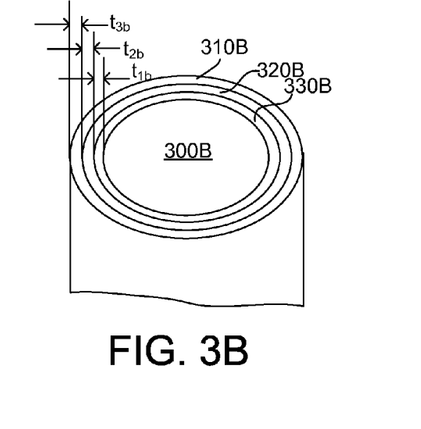
FIG. 3B is a cross sectional view of a fiber deposited with materials, according to another embodiment.

In another embodiment, an amorphous layer is deposited on the fiber before depositing the polycrystalline layer. As shown in FIG. 3B, for example, an amorphous layer 330B of $Al_2O_3$ or $SiO_2$ is first formed on fiber 300B using ALD. Subsequently, a polycrystalline layer 320B is deposited on the amorphous layer 330B. Finally, the polycrystalline layer 320B is oxidized, carbonized or nitrified to form a final layer 310B. The amorphous layer 330B has a thickness of $t_{1b}$, the polycrystalline layer 320B has a thickness of $t_{2b}$, and the oxidized, carbonized or nitrifying layer 310B has a thickness of $t_{3b}$. The thickness of $t_{1b}$ is 10 to 500 Å, the thickness of $t_{2b}$ is also 10 to 500 Å, and the thickness of $t_{3b}$ is 5 to 50 Å.

The process of depositing layers 310B, 320B, 330B may be repeated for a predetermined number of cycles to deposit sets of layers on the fiber 300B.

Instead of depositing polycrystalline material on the fiber, amorphous material may be deposited on the fiber. For example, $Al_2O_3$ may be deposited on the fiber using trimethylaluminium (TMA) as source precursor, followed by purging of TMA physisorbed on the fiber using a purge gas, and then injecting reactant precursor generated from $H_2O$, $O_3$, $O_2$ plasma or $N_2O$ plasma onto the fiber. Such layer of $Al_2O_3$ generally has $5 \times 10^9$ to $1 \times 10^{10}$ dyne/cm$^2$ of tensile stress.

The $Al_2O_3$ layer is then exposed to O* radicals and/or N* radicals generated by causing plasma on a gas including $O_2$ and $NH_3$ or $N_2O$ and $NH_3$. The percentage of $NH_3$ may be retained below 30% since excessive $NH_3$ tends to create particles that may negatively affect the deposition process. In this way, the outer periphery of the $Al_2O_3$ is converted into AlON which has an increased volume compared to $Al_2O_3$. The AlON layer is subject to compressive stress of about $1 \times 10^9$ to $5 \times 10^9$ dyne/cm$^2$.

As a result of depositing $Al_2O_3$ and AlON on the fiber, the fiber becomes more robust against bending and also stiffer. Multiple layers of $Al_2O_3$ and AlON may be deposited on the fiber in an alternating matter to afford increased resistance to bending and stiffness.

The thickness $Al_2O_3$ layer formed on the fiber may be less that 2% of the diameter of the fiber. The thickness of $Al_2O_3$ layer may be 50 Å through 300 Å.

The amorphous material may also be SiN. SiN may be deposited on a fiber using HMDS (Hexamethyldisilazane: $(CH_3)_3$—Si—NH—Si—$(CH_3)_3$) as a source precursor, and N* radicals as reactant precursor. The thickness of SiN layer may be less than 2% of the diameter of the fiber. The thickness of SiN layer may be 50 Å through 300 Å. The outer periphery of SiN layer may be exposed to O* radicals to convert the exposed portion of the SiN layer to $SiO_2$. $SiO_2$ has a higher volume compared to SiN, and therefore, compressive stress is introduced into the deposited material.

Examples of Deposition Device

Figure 4:
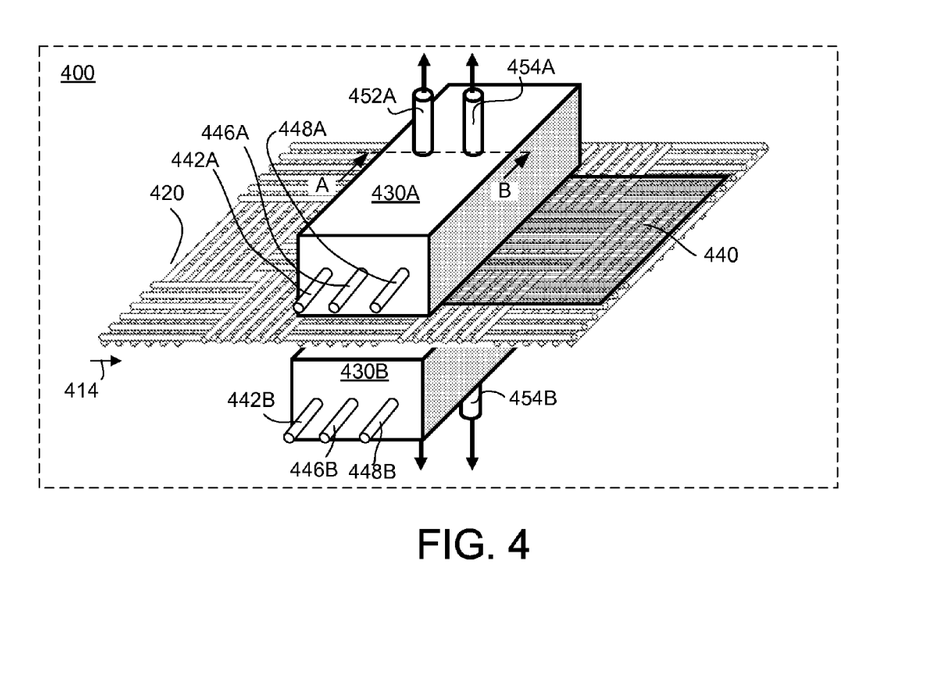
FIG. 4 is a perspective view of an apparatus for depositing materials on fibers or textiles using atomic layer deposition, according to one embodiment.

FIG. 4 is a perspective view of a deposition device 400, according to one embodiment. Although the deposition device 400 is illustrated as depositing layers of materials on a textile, the same deposition device 400 may be used to deposit layers of material on a fiber or other fiber containing materials.

The deposition device 400 may include, among other components, an upper reactor 430A and a lower reactor 430B. As textile 420 moves from the left to right (as indicated by arrow 414) and passes between the upper and lower reactors 430A, 430B, the textile 420 is deposited with a layer 440 of material. In one embodiment, the layer 440 is a polycrystalline layer, a layer formed by oxidizing, carbonizing or nitrifying the polycrystalline layer or an amorphous layer.

The entire deposition device 400 may be enclosed in a vacuum or in a pressurized vessel. Although the deposition device 400 is illustrated as depositing material on the textile 420 as the textile 420 moves horizontally, the deposition device 400 may be oriented so that the layer 440 is deposited as the textile 420 moves vertically or in a different direction.

The upper reactor 430A is connected to pipes 442A, 446A, 448A supplying precursor, purge gas and a combination thereof into the upper reactor 430A. Exhaust pipes 452A and 454A are also connected to the upper reactor 430A to discharge excess precursor and purge gas from the interior of the upper reactor 430A. The upper reactor 430A has its lower surface facing textile 420.

The lower reactor 430B is also connected to pipes 442B, 446B, 448B to receive precursor, purge gas and a combination thereof. Exhaust pipes (e.g., pipe 454B) are also connected to the lower reactor 430B to discharge excess precursor and purge gas from the interior of the lower reactor 430B. The lower reactor 430B has it upper surface facing the textile 420.

The deposition device 400 performs atomic layer deposition (ALD) on the textile 420 as the textile 420 moves from the left to the right between the lower surface of the upper reactor 430A and the upper surface of the lower reactor 430B. ALD is performed by injecting source precursor on the textile 420 followed by reactant precursor on the textile 420.

Figure 5:
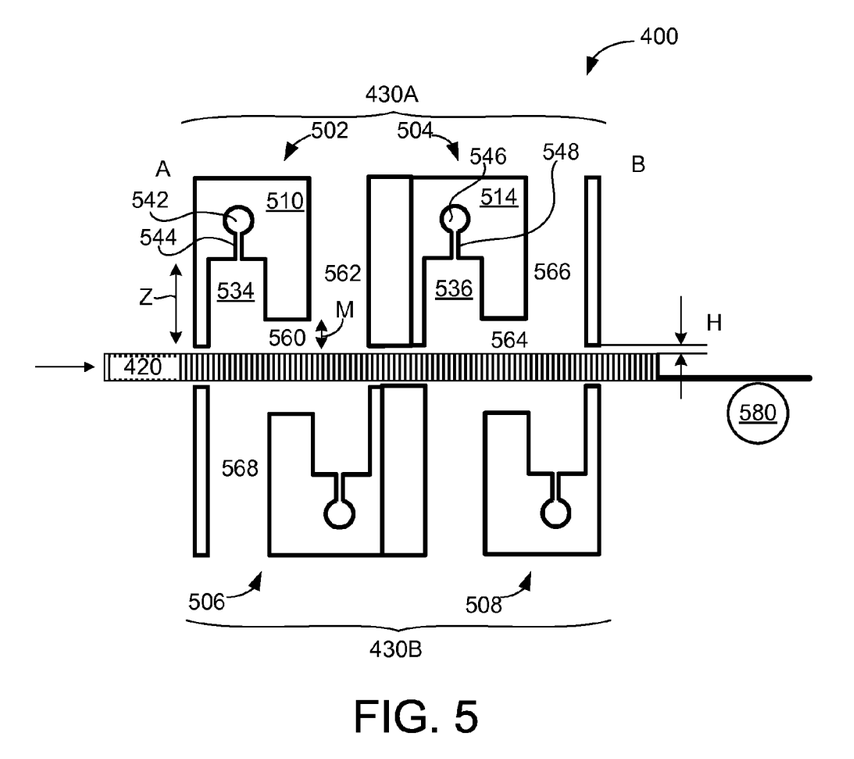
FIG. 5 is a cross sectional view of the apparatus for depositing materials on the fibers or textiles, according to one embodiment.

FIG. 5 is a cross sectional view of the deposition device 400 taken along line A-B of FIG. 4, according to one embodiment. The upper reactor 430A may include, among other components, a source injector 502 and a reactant injector 504. The source injector 502 is connected to the pipe 442A to receive the source precursor (in combination with carrier gas such as Argon) and the reactant injector 504 is connected to the pipe 448A to receive reactant precursor (in combination with carrier gas such as Argon). The carrier gas may be injected via a separate pipe (e.g., pipe 446A) or via the pipes that supply the source or reactant precursor.

The body 510 of the source injector 502 is formed with a channel 542, perforations (e.g., holes or slits) 544, a reaction chamber 534, a constriction zone 560 and an exhaust portion 562. The source precursor flows into the reaction chamber 534 via the channel 542 and the perforations 544, and reacts with the textile 120. Part of the source precursor penetrates the textile 420 and is discharged via an exhaust portion 268 formed on the lower reactor 430B. The remaining source precursor flows through the constriction zone 560 in parallel to the surface of the textile 420 and is discharged into the exhaust portion 562. The exhaust portion is connected to the pipe 452A and discharges the excess source precursor out of the injector 502.

When the source precursor flows through the constriction zone 560, excess source precursor is removed from the surface of the textile 420 due to the higher speed of the source precursor in the construction zone 560. In one embodiment, the height M of the constriction zone 560 is less than ⅔ the height Z of the reaction chamber 534. Such height M is desirable to remove the source precursor from the surface of the textile 420.

The reactant injector 504 has a similar structure as the source injector 502. The reactant injector 504 receives the reactant precursor and injects the reactant precursor onto the textile 420. The source injector 504 has a body 514 formed with a channel 546, perforations 548, a reaction chamber 536, a constriction zone 564 and an exhaust portion 566. The functions and the structures of these portions of the reactant injector 504 are substantially the same as counterpart portions of the source injector 502. The exhaust portion 566 is connected to the pipe 454A.

The lower reactor 430B has a similar structure as the upper reactor 430A but has an upper surface facing a direction opposite to the upper reactor 430A. The lower reactor 430B may include a source injector 506 and a reactor injector 508. The source injector 506 receives the source precursor via the pipe 542B and injects the source precursor onto the rear surface of the textile 420. Part of the source precursor penetrates the textile 420 and is discharged via the exhaust portion 562. The remaining source precursor flows into the exhaust portion 568 in parallel to the surface of the textile 420 and is discharged from the source injector 502.

The structure of the reactor injector 508 is substantially the same as the reactor injector 504, and therefore, detailed description thereof is omitted herein for the sake of brevity.

The deposition device 400 may also include a mechanism 580 for moving the textile 420. The mechanism 580 may include a motor or an actuator that pulls the textile 420 to the right direction as illustrated in FIG. 5. As the textile 420 is move progressively to the right, substantially the entire surface of the textile 420 is exposed to the source precursor and the reactant precursor, depositing material on the textile 420 as a result.

By having an opposing set of reactors, the source precursor and the reactant precursor flow perpendicular to the surface of the textile 420 as well as in parallel to the surface of the textile 420. Therefore, a layer of conformal material is deposited on the flat surface as well as the pores or holes in the textile 420. Hence, the material is deposited more evenly and completely on the textile 420.

In order to reduce the precursor material leaked outside the deposition device 400, the distance H between the textile 420 and the upper/lower reactor 430A, 430B is maintained at a low value. In one embodiment, the distance H is less than 1 mm, and more preferably less than tens of μms.

In one embodiment, $TiCl_4$ is used as the source precursor and $NH_3$ is used as the reactant precursor to form a polycrystalline TiN layer on the textile 420. After forming TiN layer on the textile 420, the textile may be exposed to oxygen, $H_2O$, ozone, O* radicals or a combination thereof to oxidize the surface and grain boundaries of the TiN layer into TiON.

Furthermore, inorganic material such as $SiH_4$, $SiCl_2H_2$ or organic metal compound such as hexamethyldisilazane (HMDS), tetramethyldisiloxane (TMDSO), tris(dimethylamino)silane (TDMAS) is used as source precursor, and O* radical, $H_2O$, ozone or a combination thereof is used as reactant precursor to deposit $SiO_2$ on the fiber. In order to deposit $Al_2O_3$, TMA or dimethylaluminumhydride (DMAH) may be used as the source precursor.

Figure 6:
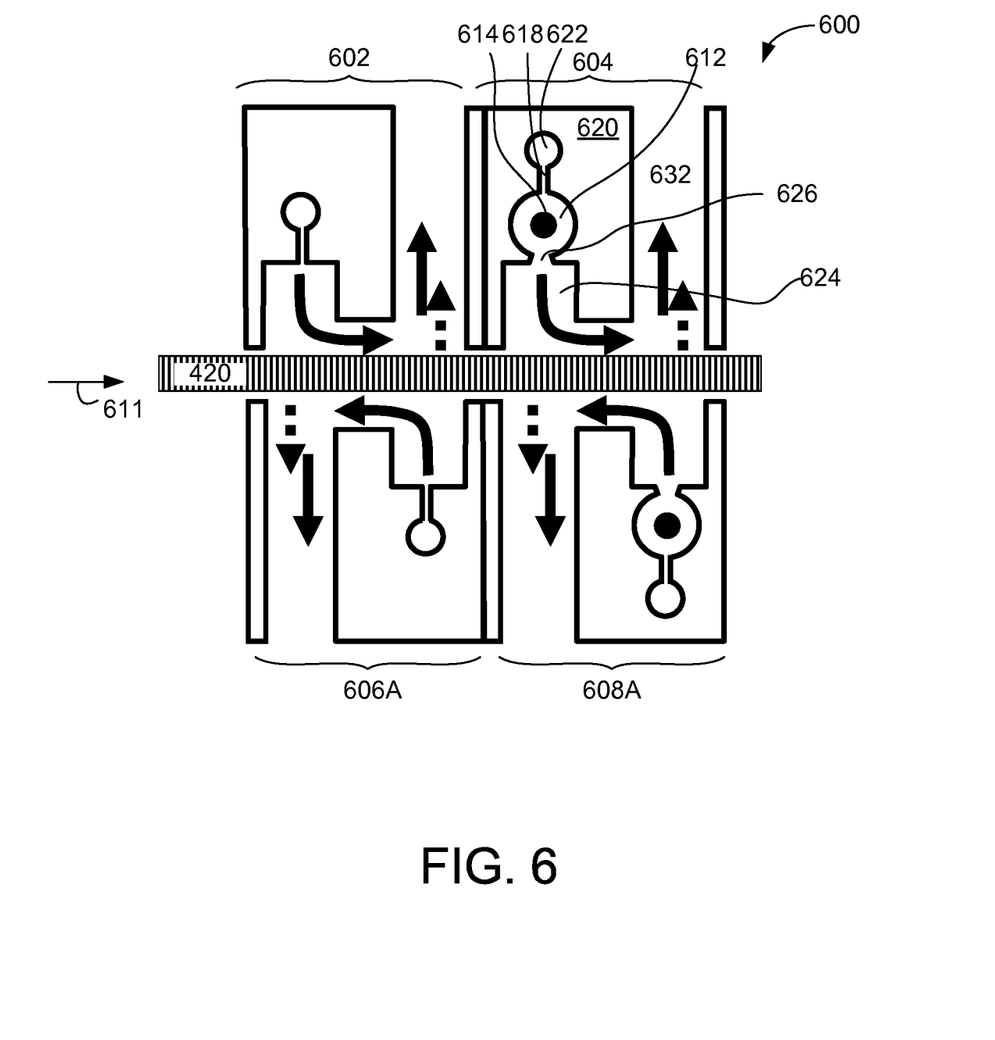
FIG. 6 is a cross sectional view of the apparatus for depositing materials on the fibers or textiles, according to another embodiment.

FIG. 6 is a cross sectional view of a deposition device 600 including radical reactors 604, 608A, according to one embodiment. The deposition device 600 is substantially the same as the deposition device 500 except that the injectors 504, 508 are replaced with the radical reactors 604, 608A.

The deposition device 600 includes source injectors 602, 606A and the radical reactors 604, 608A. The structure and function of the source injectors 602, 606A are the same as the source injectors 502, 506, and therefore, the description thereof is omitted for the sake of brevity. The textile 420 moves from the left to the right as shown by arrow 611 in FIG. 6 so that the textile 420 is exposed first to the source precursor (by the source injectors 602, 606A) and then the radicals (by the radical reactors 604, 608A).

The radical reactor 604 may include, among other components, an inner electrode 614 and a body 620. The body 620 may be formed with, among other structures, a channel 622, perforations (e.g., holes or slits) 618, a plasma chamber 612, an injection holes 626, a reaction chamber 624 and an exhaust portion 632. Gas is provided into the plasma chamber 612 via the channel 622 and the perforations 618. Voltage difference is applied between the inner electrode 614 and the body 620 of the radical reactor 604 to generate plasma within the plasma chamber 612. The body 620 of the radical reactor 604 functions as an outer electrode. In an alternative embodiment, an outer electrode separate from the body 620 may be provided to surround the plasma chamber 612. As a result of generating the plasma, radicals of the gas is formed in the plasma chamber 612 and injected into the reaction chamber 624 via the injection holes 626.

As described above with reference to FIG. 5, part of the radicals generated by the radical reactors 604, 608A penetrate the substrate and are discharged by exhaust portions provided in the radical reactors of the opposite side. The other radicals flow in parallel to the surface of the textile 420 and are discharged by the exhaust portions of the radical reactor that generated the radicals.

In one embodiment, the radical reactors 604, 608A generates and injects N* radicals as reactant precursor onto the textile 420 previously injected with source precursor including $TiCl_4$ to form a polycrystalline TiN layer on the textile 420.

In one embodiment, the radical reactors 604, 608A generate and inject O* radicals as reactant precursor onto the textile 420 previously injected with source precursor including inorganic material such as $SiH_4$, $SiCl_2H_2$ or organic metal compound such as hexamethyldisilazane (HMDS), tetramethyldisiloxane (TMDSO), tris(dimethylamino)silane (TDMAS) to deposit $SiO_2$ on the fiber. Similarly, O* radicals may be injected as the reactant precursor onto the textile 420 previously injected with source precursor including trimethylaluminium (TMA) or dimethylaluminumhydride (DMAH) to deposit $Al_2O_3$ on the textile 420.

Fibers or fiber containing materials may be processed by the depositing devices 500, 600 to deposit materials on the fibers or the fiber containing material. Furthermore, the same textile, fibers, yarn or other component structures may undergo repeated processes at the depositing devices 500, 600 to deposit multiple sets of layers on the fibers or the fiber containing material.

Devices for depositing materials on the fibers or the fiber containing material are described above with reference to FIGS. 4 through 6 are merely illustrative. Various other devices may be used to deposit materials on the fibers of the fiber containing material.

Examples Method of Depositing Material

Figure 7:
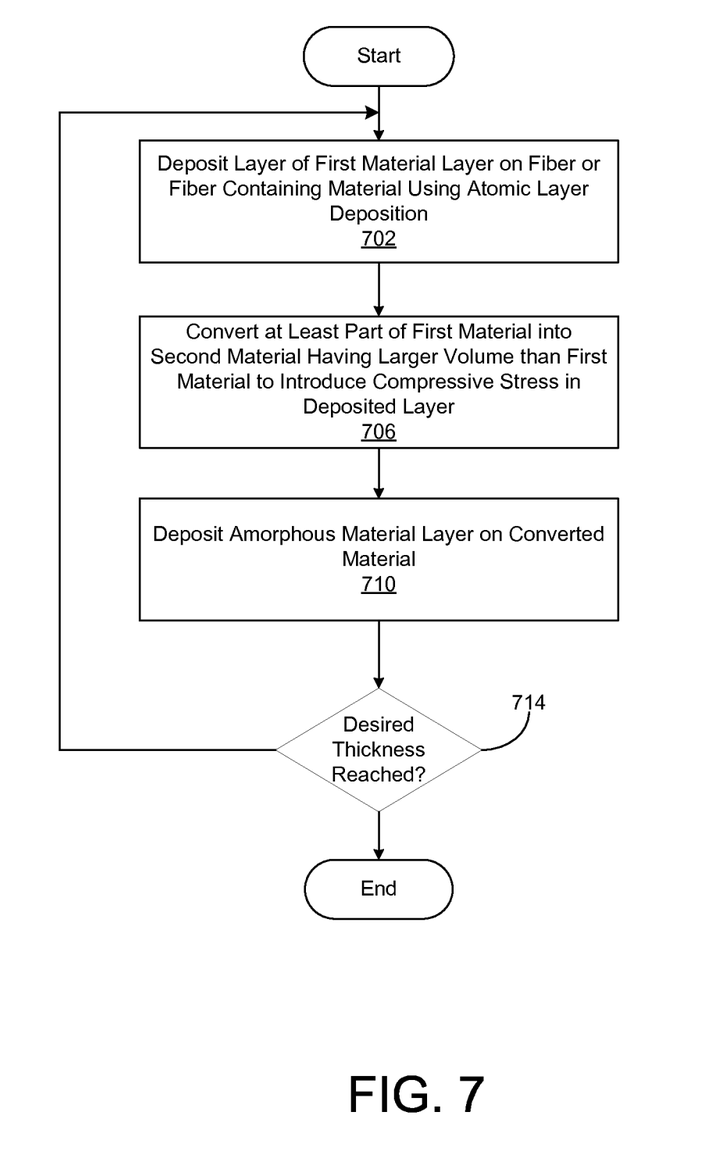
FIG. 7 is a flowchart illustrating a method of depositing materials on a fiber or a fiber containing material, according to one embodiment.

FIG. 7 is a flowchart illustrating a method of depositing materials on the fibers or fiber containing material, according to one embodiment. First, a layer of first material layer is deposited 702 on a fiber or a fiber containing material using ALD. For this purpose, a depositing device described above with reference to FIGS. 4 through 6 may be used. The first material may be polycrystalline material such as TiN or amorphous material such as $Al_2O_3$ or $SiO_2$.

After a layer of first material is deposited on the fiber or the fiber containing material, at least part of the first material is converted 706 into second material that has larger volume than the first material to introduce compressive stress in the layer. The conversion may oxidizing, nitrifying or carbonizing of the first material. The second material may include, for example, TiON when the first material is TiN.

Then an amorphous material layer may be deposited 710 on the oxidized, nitrified or carbonized surface of the polycrystalline material layer. The amorphous material layer may include, for example, $Al_2O_3$ or $SiO_2$. In this way, the amorphous layer may be subject to tensile stress and combination of differently stressed films will increase the stiffness of the fiber or the fiber containing material, and the outer most layer should have compressive stress for the increased rigidity on the fibers or fiber containing materials.

It is then determined 714 whether the thickness of deposited materials is sufficient. If the thickness of the deposited materials is not sufficient, the process returns to depositing 702 a layer of first material on the fiber or the fiber containing material. If the thickness of the deposited materials is sufficient, then the process terminates.

The process illustrated in FIG. 7 is merely illustrative. Alternatively, certain steps in FIG. 7 may be omitted. For example, depositing 710 of the amorphous layer may be performed before depositing a polycrystalline material layer on the fiber or the fiber containing material. Alternatively, depositing 710 of the amorphous material layer may be omitted.

Depositing Material for Other Functionality

In lieu of or in addition to coating materials to increase rigidity or strength, the fiber or the fiber containing material may be coated with material to lower the emissivity of the fibers, yarn or textile. The emissivity is a property of a material related to emission of energy from its surface relative to other materials. In applications such as military uniforms, it is advantageous to lower the emissivity of the fiber or fiber containing material to prevent detection of the person wearing the military uniform by night vision. To lower the emissivity, the fiber or the fiber containing material may be coated with paint to reduce the emissivity of the uniform. However, the effect of the paint may not endure for a long time since the paint may be become peeled off or removed during washing or repeated use of the uniform.

In one embodiment, aluminum is deposited on the fibers, yarn or textile using ALD to lower emissivity. For this purpose, DMAH (DimethylaluminumHydride) may be used as a source precursor and hydrogen plasma may be used as a reactant precursor. Aluminum deposited using ALD is bonded securely to the fibers, yarn or textile. Hence, the decreased emissivity persists for a longer duration compared to coating of paint on textile.

Fibers may be deposited with material to isolate the fibers from moisture or oxygen. Carbon fibers, for example, are used as heating components in heaters due to its high electric conductivity. However, these fibers may react with moisture or oxygen at a high temperature (e.g., 300° C.) and oxidize. Therefore, materials such as $Al_2O_3$ may be deposited on the carbon fibers to prevent the carbon fibers from oxidizing at a high temperature. $Al_2O_3$ may be deposited on the fibers, for example, by using trimethylaluminium (TMA) or dimethylaluminumhydride (DMAH) as the source precursor and O* radical, $H_2O$, ozone or a combination thereof as reactant precursor.

Example Use of Fibers, Yarn or Textile Deposited with Material

The fibers, yarn or textile deposited with polycrystalline material and its corresponding carbonized, nitrified or oxidized layer may be used to form fabric. Such form can be cut and shaped into wearable clothes. One of such wearable clothes is military uniforms or bullet proof vests. The same fibers, yarn or textile may be coated with low emissive material, as described above, to decrease the chance of detection by night vision cameras. Alternatively, different fibers, yarn or textile coated with low emissive material may be used in conjunction with the fibers, yarn or textile deposited with polycrystalline material for to fabricate clothes with enhanced strength and rigidity as well as lower detection by night vision cameras.

The fibers, yarn or textile deposited with polycrystalline material and its corresponding carbonized, nitrified or oxidized layer may be used as component for composite material. For example, the fibers, yarn or textile coated with the polycrystalline material may be used in carbon-fiber-reinforced polymer (CFRP).

Although the present invention has been described above with respect to several embodiments, various modifications can be made within the scope of the present invention. Accordingly, the disclosure of the present invention is intended to be illustrative, but not limiting, of the scope of the invention, which is set forth in the following claims.

What is claimed is:

1. A method of depositing material on a fiber or a fiber containing material, comprising:

injecting source precursor from a source injector onto a portion of the fiber or the fiber containing material;

causing a relative movement between the fiber or the fiber containing material and the source injector;

injecting reactant precursor from a reactant injector onto the portion of the fiber or the fiber containing material to deposit a layer of first material subject to tensile stress by atomic layer deposition (ALD); and converting at least an outer portion of the layer to a second material having larger volume compared to the first material to induce compressive stress in the layer.

2. The method of claim 1, wherein the first material comprises polycrystalline material and the conversion comprises oxidizing, nitrifying or carbonizing at least part of grain boundaries and a surface of the polycrystalline material.

3. The method of claim 2, wherein the polycrystalline material comprises at least one of semiconductor, metal compound or metal.

4. The method of claim 2, wherein the polycrystalline material comprises TiN.

5. The method of claim 2, further comprising depositing a layer of amorphous material on the surface of the second material.

6. The method of claim 5, wherein the amorphous material comprises at least one of $Al_2O_3$ or $SiO_2$.

7. The method of claim 1, wherein the reactant precursors comprise radicals generated by exposing gas to plasma.

8. The method of claim 1, wherein the first material comprises amorphous material and the conversion comprises oxidizing, nitrifying or carbonizing at least part of the first material.

9. The method of claim 8, wherein the amorphous material comprises at least one of $Al_2O_3$ and SiN.

10. A method of depositing material on a fiber or a fiber containing material, comprising:

injecting source precursor from a source injector onto a portion of the fiber or the fiber containing material;

injecting reactant precursor from a reactant injector onto the portion of the fiber or the fiber containing material to deposit a layer of amorphous material subject to tensile stress by atomic layer deposition (ALD); and converting at least an outer portion of the layer to a second material having larger volume compared to the first material to induce compressive stress in the layer by oxidizing or nitrifying at least the outer portion of the layer.

11. The method of claim 10, wherein the layer of amorphous material is a layer of amorphous SiN.

* * * * *